(12) United States Patent
Sethumadhavan et al.

(10) Patent No.: US 10,482,999 B2
(45) Date of Patent: Nov. 19, 2019

(54) SYSTEMS AND METHODS FOR EFFICIENT HANDLING OF MEDICAL DOCUMENTATION

(71) Applicant: APIXIO, INC., San Mateo, CA (US)

(72) Inventors: Vishnuvyas Sethumadhavan, Mountain View, CA (US); Robert Derward Rogers, Pleasanton, CA (US); John O. Schneider, Los Gatos, CA (US); Erin Michelle Faverty, San Carlos, CA (US); Austin Robert Rogers, Pleasanton, CA (US); Shahram Shawn Dastmalchi, San Ramon, CA (US)

(73) Assignee: APIXIO, INC., San Mateo, CA (US)

( * ) Notice: Subject to any disclaimer, the term of this patent is extended or adjusted under 35 U.S.C. 154(b) by 1080 days.

(21) Appl. No.: 14/543,738

(22) Filed: Nov. 17, 2014

(65) Prior Publication Data

US 2015/0142473 A1    May 21, 2015

Related U.S. Application Data

(60) Provisional application No. 61/905,806, filed on Nov. 18, 2013.

(51) Int. Cl.
*G16H 10/60* (2018.01)
*G06F 19/00* (2018.01)

(52) U.S. Cl.
CPC ........... *G16H 10/60* (2018.01); *G06F 19/328* (2013.01); *G06F 19/324* (2013.01)

(58) Field of Classification Search
CPC .... G06F 19/322; G06F 19/328; G06F 19/324; G16H 10/60; G16H 10/00; G16H 10/20;
(Continued)

(56) References Cited

U.S. PATENT DOCUMENTS 7,321,861 B1    1/2008  Oon
2002/0188182 A1*  12/2002  Haines ................ A61B 5/0002
                                                                  600/300
(Continued)

FOREIGN PATENT DOCUMENTS

KR    10-2009-0050881    5/2009

OTHER PUBLICATIONS

Korean Intellectual Property Office, ISA, "International Search Report and Written Opinion" in PCT Application No. PCT/US2012/053182, dated Mar. 18, 2013, 12 pages.
(Continued)

*Primary Examiner* — Linh Giang Le
(74) *Attorney, Agent, or Firm* — Kang S. Lim

(57) ABSTRACT

Systems and methods for efficient medical chart review are provided. In some embodiments, medical records are received. The admissibility of each record is then determined. Next, a condition and MEAT assessment is generated for the medical records. The condition and MEAT determination each have a corresponding confidence. A determination may be made whether human quality assurance is required. If so, the medical records may be routed to one or more coders for human review. In addition, the systems and methods may also perform an audit analysis on the records, which identifies codes which have been submitted and have insufficient evidence. Lastly, a cost metric for the patient based upon the condition and MEAT determination may be generated.

24 Claims, 16 Drawing Sheets

(58) Field of Classification Search
CPC ........ G16H 10/40; G16H 10/65; G16H 15/00;
G16H 20/00; G16H 20/10; G16H 20/13;
G16H 20/17; G16H 20/30; G16H 20/40;
G16H 20/60; G16H 20/70; G16H 20/90;
G16H 30/00; G16H 40/00; G16H 40/20;
G16H 40/40; G16H 40/60; G16H 40/63;
G16H 40/67; G16H 50/00; G16H 70/00;
G16H 70/20; G16H 70/40; G16H 70/60;
G16H 80/00

See application file for complete search history.

(56) References Cited

U.S. PATENT DOCUMENTS

| | | |
|---|---|---|
| 2005/0043986 A1 | 2/2005 | McConnell |
| 2005/0138017 A1 | 6/2005 | Keen et al. |
| 2006/0036619 A1 | 2/2006 | Fuerst et al. |
| 2006/0047669 A1 | 3/2006 | Durrence et al. |
| 2006/0129435 A1 | 6/2006 | Smitherman et al. |
| 2007/0016450 A1 | 1/2007 | Bhora et al. |
| 2007/0055545 A1 | 3/2007 | Maughan et al. |
| 2007/0219829 A1* | 9/2007 | Kay ............... G06F 19/322 705/3 |
| 2008/0091633 A1 | 4/2008 | Rappaport et al. |
| 2008/0120296 A1 | 5/2008 | Kariathungal et al. |
| 2008/0263048 A1 | 10/2008 | Wise |
| 2008/0270340 A1 | 10/2008 | Abrams et al. |
| 2009/0024615 A1 | 1/2009 | Pedro et al. |
| 2009/0070103 A1 | 3/2009 | Beggelman et al. |
| 2009/0112882 A1 | 4/2009 | Maresh et al. |
| 2009/0136102 A1 | 5/2009 | Kimpe et al. |
| 2009/0271221 A1 | 10/2009 | Aridi et al. |
| 2010/0117799 A1 | 5/2010 | Dormer et al. |
| 2010/0131299 A1 | 5/2010 | Hasan et al. |
| 2010/0169123 A1 | 7/2010 | Maus et al. |
| 2010/0179827 A1 | 7/2010 | McCallie, Jr. et al. |
| 2010/0185496 A1 | 7/2010 | Hahn et al. |
| 2010/0324936 A1 | 12/2010 | Vishnubhatla et al. |
| 2011/0078145 A1 | 3/2011 | Chung et al. |
| 2012/0066017 A1 | 3/2012 | Siegel |
| 2012/0284056 A1* | 11/2012 | Hofstetter ............ G06F 19/322 705/3 |
| 2013/0159023 A1* | 6/2013 | Srinivas ............... G06Q 50/22 705/4 |
| 2013/0297536 A1* | 11/2013 | Almosni ............... G06F 19/345 706/12 |
| 2014/0278832 A1 | 9/2014 | Glavina |

OTHER PUBLICATIONS

USPTO, ISA/US, "Notification of Transmittal of the ISR and the Written Opinion of the International Searching Authority, or the Declaration," in PCT Application No. PCT/US14/66196, dated Apr. 2, 2015, 8 pages.

* cited by examiner

Fig. 15

SYSTEMS AND METHODS FOR EFFICIENT HANDLING OF MEDICAL DOCUMENTATION

CROSS-REFERENCE TO RELATED APPLICATIONS

This non-provisional application claims the benefit of and is a continuation-in-part of U.S. provisional application No. 61/905,806 filed on Nov. 18, 2013, of the same title, which application is hereby fully incorporated in its entirety by this reference.

BACKGROUND

The present invention relates generally to systems and methods for efficient handling of medical records via automated chart review processes. The present systems and methods enables more accurate and efficient identification of medical conditions, confirms the presence of documentation MEAT (Monitor, Evaluate, Assess and Treat), ensures human QA if effectively performed, minimizes auditing risk, and calculates costs/risks for patients.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is that human intervention is required to perform medical chart reviews. Reviewing medical charts is a time consuming and labor intensive process, whereby trained individuals review the documents in order to ensure the documents are admissible, identify conditions found within the charts (for billing purposes), and ensuring other required information is present in the document in order to bill appropriately. One major aspect of this chart review process includes medical coding (also known as clinical coding, diagnostic coding or health care coding), accuracy assurance, identification of MEAT data within documents, and the like.

In order to ensure chart review is done accurately, redundancy of review is built into the manual systems currently employed. These redundancies further exacerbate the time and effort required for chart review. Moreover, despite these precautions, chart review is still often subject to erroneous or incomplete analysis.

It is therefore apparent that an urgent need exists for an efficient means for reviewing medical charts. Such systems and methods enable more efficient identification of admissible medical documents, condition classification, MEAT classification, and audit protection. Such systems and methods may also increase efficiency of human quality assurance steps, and risk analysis.

SUMMARY

To achieve the foregoing and in accordance with the present invention, systems and methods for efficient medical chart review are provided. In particular, systems and methods for chart review is provided which can automatically generate condition classification, and MEAT classifications, with confidence intervals, in order to provide more accurate, efficient and rapid review of charts.

In some embodiments, the systems and methods receive medical records. The admissibility of each record is then determined. Admissibility is determined by confirming that the medical record was generated from a face-to-face encounter, confirming signature, and confirming the specialist generating the medical record is authorized to make the corresponding diagnosis. Next, a condition and MEAT assessment is generated for the medical records. The condition and MEAT determination each have a corresponding confidence. Generating the condition and MEAT determination includes keyword and contextual analysis.

After condition and MEAT have been analyzed for, a determination may be made whether human quality assurance is required. If so, the medical records may be routed to one or more coders for human review. A summary of the condition and MEAT analysis is likewise generated. The summary includes graphically highlighting evidence within each medical record for the coder.

The determination of whether human quality assurance is desired is based on the confidence values, as well as medical record attributes. These attributes may include the condition, geography of the medical record, physician who generated the medical record, insurance type, and patient history. The routing of the medical records is done to maximize a goal. This may be accomplished by referencing a profile for each coder, and selecting one which will best effectuate the goal.

In addition, the systems and methods may also perform an audit analysis on the records. This analysis includes identifying codes which have been submitted and have insufficient evidence, and analyzing specific medical records with submitted codes to determine if sufficient evidence is present. If there is time to amend the medical records, a suggestion to amend to cure deficiencies may be generated. Otherwise, a suggestion for a follow-up with the patient may be generated when the medical records cannot be amended.

Lastly, a cost metric for the patient based upon the condition and MEAT determination may be generated.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIG. 15 illustrates an example screenshot of a medical document where evidence has been highlighted for reviewer consumption, in accordance with an embodiment.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Note that, for the purposes of this disclosure, the term "finding", "opportunity" or "work" may be utilized interchangeably in order to signify work which is assigned to coders for annotation with medical codes. This work includes providing medical records to the coder for which they can identify the medical findings and extrapolate codes for them.

Figure 1:
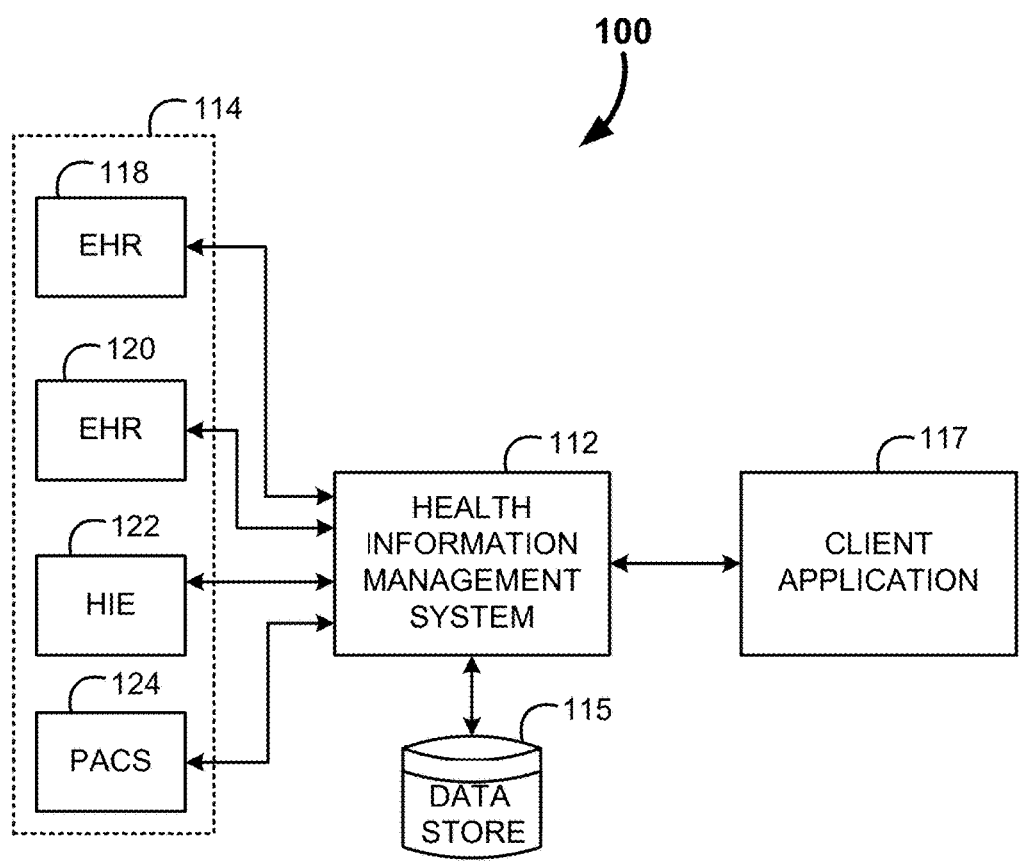
FIG. 1 shows a medical system, in accordance with an embodiment.

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include an electronic health record (EHR) 118, EHR 120, health information exchange (HIE) 122, and a picture archiving and communication system (PACS) 124. Of course, additional records may be included within the medical information sources 114.

"Medical information", as used herein, may refer to any health-related information, including but not limited to patient medical records, patient entered information, care team entered information, healthcare device generated information, and billing information. Also note that the terms "documents", "evidence", and "record" all refer to pieces of medical information, which may be collected together into a medical chart for a patient.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. In some methods and embodiments, information that is extracted from images is tagged to enhance recall of search queries. Indexing, at least in part, processes document and converts them into formats that allows for quick searching across a large collection of documents.

In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
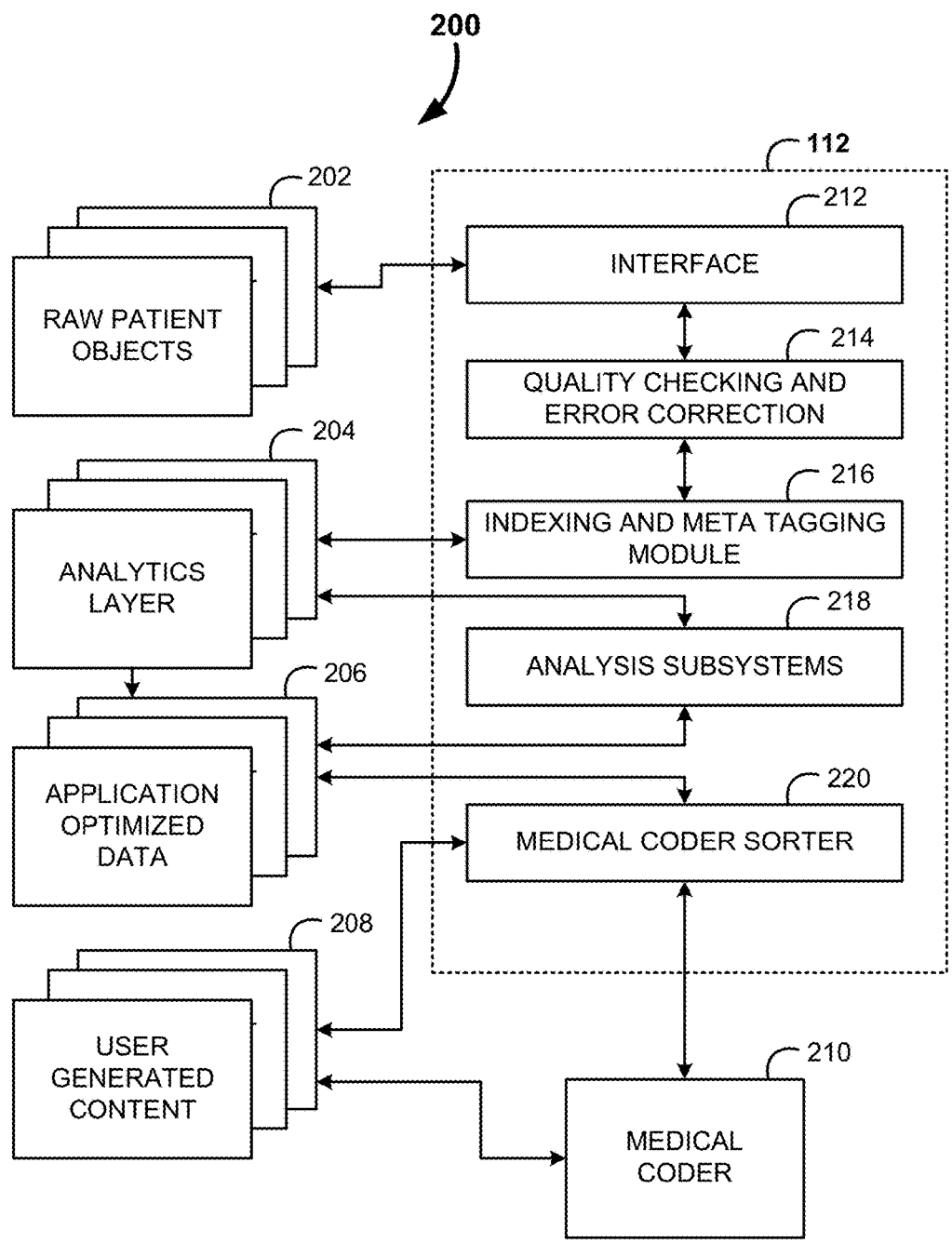
FIG. 2 shows further details of the system within a data architecture, including analysis subsystems and a medical coder sorter, in accordance with an embodiment.

Turning to FIG. 2, a more detailed illustration for the health information management system 112 is provided. In this example diagram, the health information management system 112 is interacting with multiple levels of data storage, shown generally at 200. The storage level begins with raw patient objects 202 which are received from the plurality of sources 114.

The health information management system 112 includes an interface 212 which can collect these objects. These objects 202 may be collected in various forms, such as but not limited to text, html, CCD, CCR, HL7 and any other type or formatted information. The interface 212 then provides to the information to a quality checking and error corrector 214, in some embodiments.

The quality checking and error corrector 214 may simply delete duplicate errors and redundant patient medical records, such as, multiple records for the same individual appearing as though the records are for different individuals or multiple data elements that are recorded similarly but slightly differently in the different sources. The quality checking and error corrector 214 may also perform other basic and known error correction processes. Alternatively, more advanced quality checking and error corrector 214 systems may check the quality of medical information provided by various sources 114 by the patients, structured data, and unstructured data, in a Wiki-like mannered setting whereby the users can help maintain and improve the quality of information displayed.

In some embodiments, an indexing and Meta tagging module 216 may utilize a processor to processing the data, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others. The processed data may then be provided to the second level of the data storage architecture, the analytics layer 204. In some embodiments, the analytics layer 204 may be transient.

Analytical subsystems 218, as described further below, may take information from the analytics layer 204 and perform certain tasks on the information, which may include query, search, presentation, and quality checking. The output of the analytics 218 may be stored within the third layer of the data architecture, which is known as the application optimized data 206. The analytical subsystems 218 may be configured, in some embodiments, to determine admissibility of the medical records, classify patient conditions, analyze the records for MEAT (Monitor, Evaluate, Asses, and Treat) parameters, and generate audit and cost metrics.

In some embodiments, the medical coder sorter 220 accesses data that has been optimized for it, and determines whether to provide a finding to the medical coder 210. The medical coder 210 may code the finding and provide that data into a fourth level of the data architecture, which includes all user generated content 208. In some embodiments, the medical coder sorter 220 also generates reports about coding and coders which likewise may be stored in the user generated content 208 layer.

Figure 3:
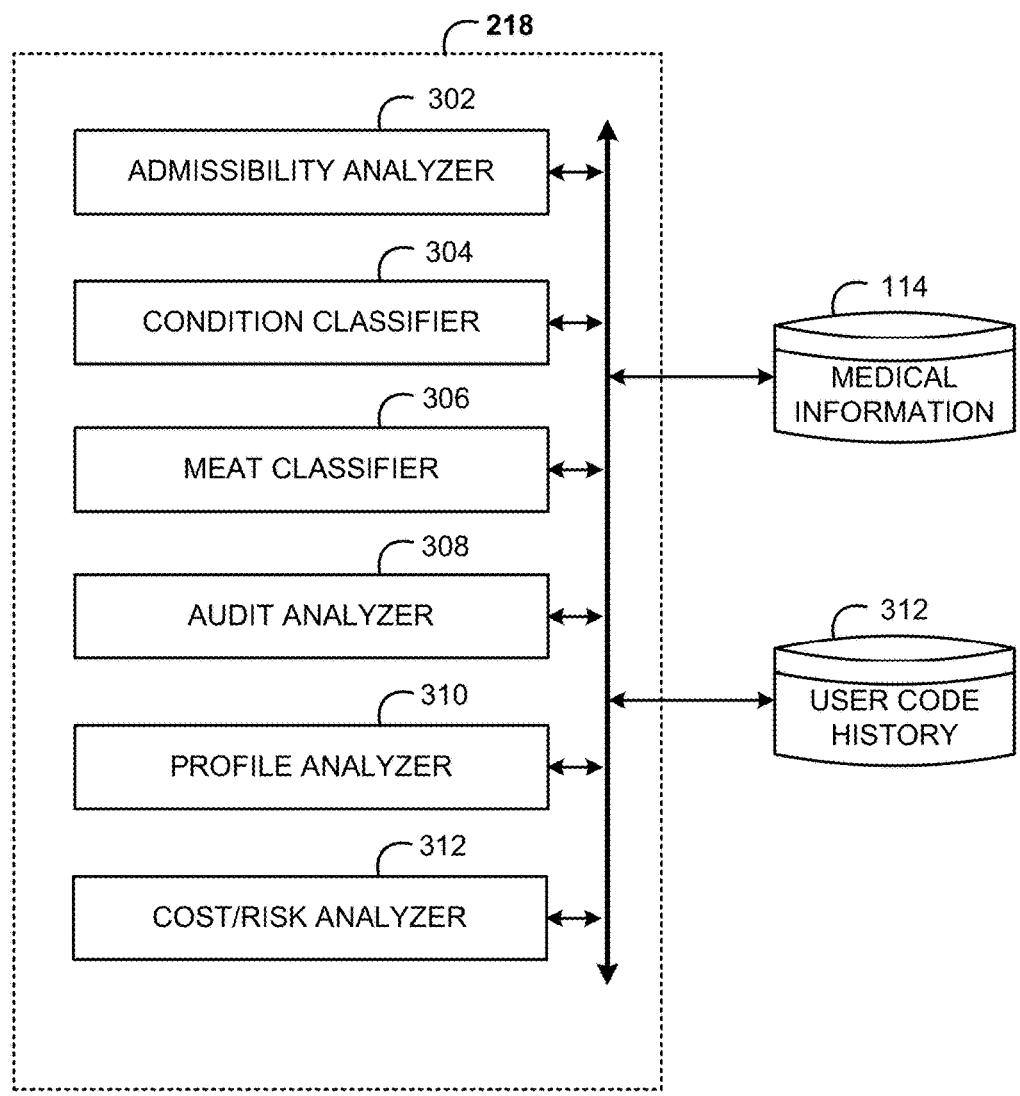
FIG. 3 shows an exemplary embodiment of the analysis subsystems, in accordance with an embodiment.

Turning to FIG. 3, a more detailed illustration of the analytical subsystems 218 is provided. Here it can be seen that the analytical subsystems 218 includes a variety of constituent modules, including a admissibility analyzer 302, a condition classifer 304, a MEAT classifier 306, an audit analyzer 308, a profile analyzer 310 and a cost/risk analyzer 312. Each of these subsystems may interface with the medical information 114 and user coding history 312 (for medical coders) in order to perform their respective functions.

Figure 4:
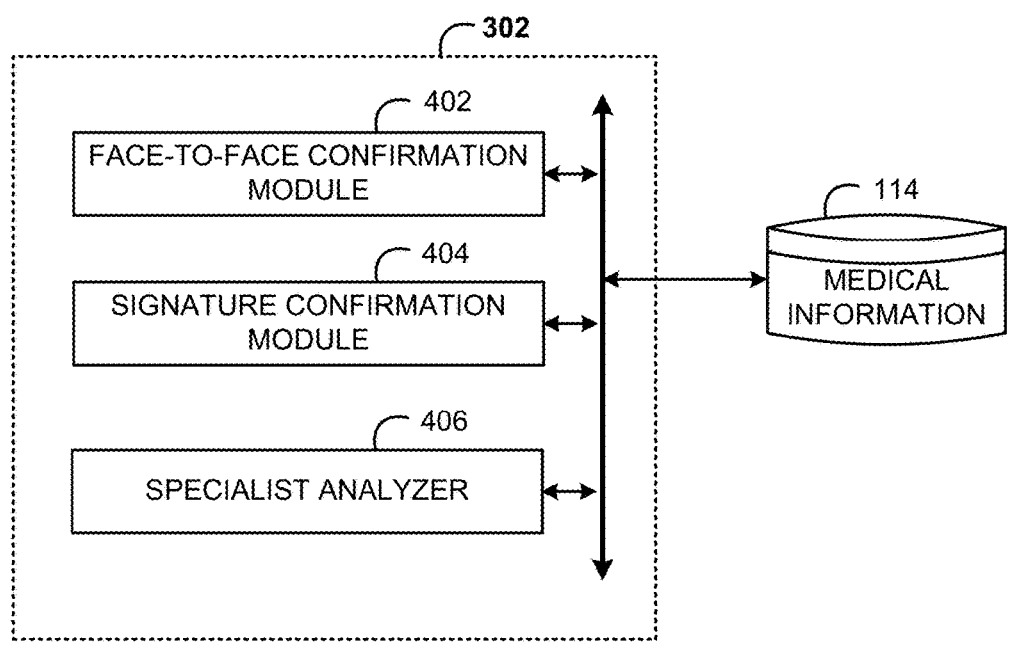
FIG. 4 shows an exemplary embodiment of the admissibility analyzer, in accordance with an embodiment.

In order for a medical record to be submitted to Medicare for reimbursement for a condition, regulations require that the medical record be admissible. The admissibility analyzer 302 ensures that medical information 114 being reviewed meets these admission requirements. FIG. 4 provides a more detailed view of the admissibility analyzer 302. The analyzer includes three subsystems, including a face-to-face confirmation module 402, a signature confirmation module 404 and a specialist analyzer 406.

In order for a medical record to be admissible it needs to be the result of a face-to-face encounter between the physician and the patient. The face-to-face confirmation module 402 identifies contextual clues within the document to ensure that this requirement has been met. This may include explicit statements, such as "patient arrived at the clinic at 2:00", or may include inferences of the patient being present. For example, the medical record could indicate that the patient had blood drawn as part of the diagnosis, which requires the patient being present. Additionally, document metadata may be employed to make this determination.

Additionally, a document is not admissible unless it has been signed by the physician. The signature confirmation module 404 may utilize image recognition algorithms to ensure a signature is present. Advanced embodiments, may even perform signature matching between the document and a repository of signatures to ensure the document is authentic. Additionally, document metadata may be employed to make this determination.

The specialist analyzer 406 addresses that certain conditions can only be validly diagnosed by specific physicians. For example, a podiatrist may be able to diagnose conditions that an oncologist is not allowed to, and vice versa. This module compares the physician specialty to the condition (as determined below) and compares the match to a table of allowable diagnoses for the specialist.

If any of the above conditions for document admissibility are not present, then the document may be precluded from further analysis. Further, in some cases, the system may be able to identify to the healthcare provider, physician, or insurance company what the deficiency is regarding the medical record, and provide suggestions in order to cure such deficiency. For example, if a document is missing a signature, the physician may be contacted to include the missing signature.

In some cases the admissibility of a document may be determined using the following equation:

$$\text{Admissibility} = \text{logistic}(\text{feature vector} - \text{weight vector})$$

Wherein the feature vector includes the condition events, face to face conditions, and MEAT events. In some embodiments the Admissibility equation may be the following:

$$\text{Admissibility} = (\text{condition event} \cap \text{code-conditions} \neq 0)$$

and $$(\text{Face-to-face Event} == \text{True})$$

and $$(\text{MEAT events} \neq 0)$$

Returning to FIG. 3, the condition classifier 304 utilizes keyword searching and contextual analysis in order to determine likely conditions for the patient. In addition to the identification of the condition, the classifier may generate a confidence measure for the condition. For example, the one document may include the phrase "100 mg metformin bid", which is a treatment for diabetes. This may cause the condition classifier 304 to classify the condition as diabetes with a relatively low confidence metric. However, if the document also includes the words "PMH: Diabetes" and "labs:HgA1c=9.2", then the condition of diabetes would be presented as having a much higher confidence score.

Likewise, the MEAT classifier 306 may utilize keyword and contextual searches to identify MEAT (Monitor, Evaluate, Assess and Treat) within a medical record. MEAT must be found within a medical record in order for it to be admissible. As such, the MEAT classifier identifies these properties within the document and assigns a confidence score as well. For example, the document may include the term "PMH: Diabetes" which would qualify the monitor property. Likewise, "labs:HgA1c=9.2" qualifies as an evaluation component. The record may also include "Diabetes, status stable" which covers the assessment component. Lastly, the phrase "continue metformin, rtc in 3 mo" would satisfy the treatment component.

Figure 5:
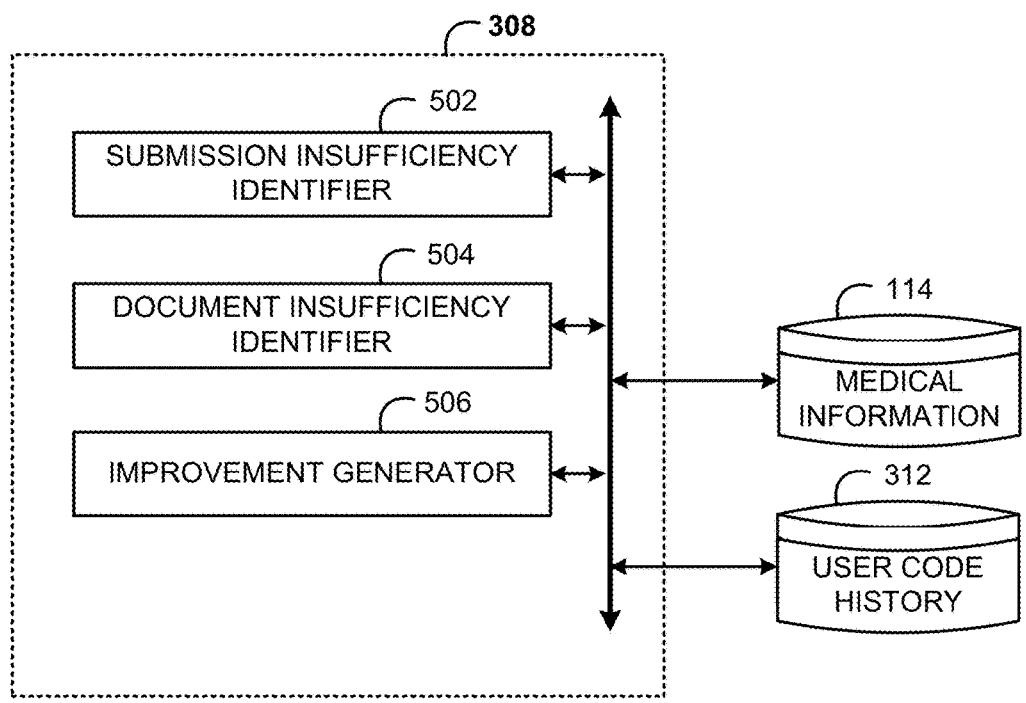
FIG. 5 shows an exemplary embodiment of the audit analyzer, in accordance with an embodiment.

After condition and MEAT classification, an audit analyzer 308 may determine what the risk of an audit is, and provide suggestions to mitigate auditing risk. FIG. 5 provides a more detailed view of the audit analyzer 308. In this example, a submission insufficiency identifier 502 may use the MEAT classifier results and identify which codes have already been submitted to a risk assessment authority (Medicare, HHS, etc.) that have insufficient documentation. Likewise, a document insufficiency identifier 504 may look at a specific document that corresponds to a submitted code to determine if it contains sufficient documentation. These determinations of whether sufficient documentation exists may include comparing the confidence measures against thresholds, in some embodiments.

Once insufficiencies have been determined, an improvement generator 506 may determine appropriate remedial measures to minimize the risk. This includes suggesting that documents are amended to include deficient information (if there is still time to amend the document), or generate additional encounter data which better supports the submitted code.

Likewise, by using condition classifier data, conditions that are identified as probably existing, but which have insufficient documentation to be submitted, may be flagged and suggestions may be generated in order to prompt the health care provider to generate the additional documentation. In some cases this may include asking the patient to come in for additional examination in order to generate the needed data. Likewise, this information may be utilized to improve internal processes at the health care provider in order to avoid documentation inadequacies in future encounters.

In some cases, auditing can be performed live, as soon as medical information becomes available. In other cases, the auditing may be performed as a batch process on a schedule.

Returning to FIG. 3, the profile analyzer 310 may compare metrics of individual coders within an organization, as well as metrics that apply to the organization as a whole, in order to generate profiles for the customer (healthcare provider, network, insurance company, etc.) and for users. For individual users/coders, their annotations and findings when presented a medical record may be compared against peers to determine the coder's accuracy and other metrics (speed, specific document types they have issues with, medical knowledge by topic, propensity to over or under code, economic gain, process waste, etc.). In addition, users may be presented with different standards (e.g., documents for which internal or external coding standards have been developed), and the coder's results are compared against the standards to generate a coder profile.

In addition to determining coder speed, accuracy, propensity to over or under code, additional attributes can be determined, such as performance variation over time, application domains, and the like. Coder profiles may be consolidated for an entity and combined with other statistical data (process waste, labor skill, underlying disease prevalence, etc.) to generate a customer profile. For example, an insurance provider profile may include relative frequency of a specific condition within its policy holders.

Profiles, once generated may be utilized to ensure routing of healthcare records is optimized, and further may be displayed to the coder's and/or customer. Gold standards for customers may be developed by using customer expert use application. These profiles may drive performance reviews, goal setting, training and investments.

In addition to profile generation, the analytical subsystems 218 additionally include a cost/risk analyzer 312. Health care codes, which are typically generated in order to submit for Medicare reimbursement, are actually poor indicators of the cost/risk present in a patient population. By employing MEAT classifications and condition classification, as well as other contextual metrics, more accurate measures of risk and costs may be predicted via a calculation that correlates a cost surrogate (such as a health care code and diagnostic context) with a measure of importance, within an information stream. These costs may be presented as direct costs to the customer (insurance company, healthcare provider, etc.) or as indirect costs.

Figure 6:
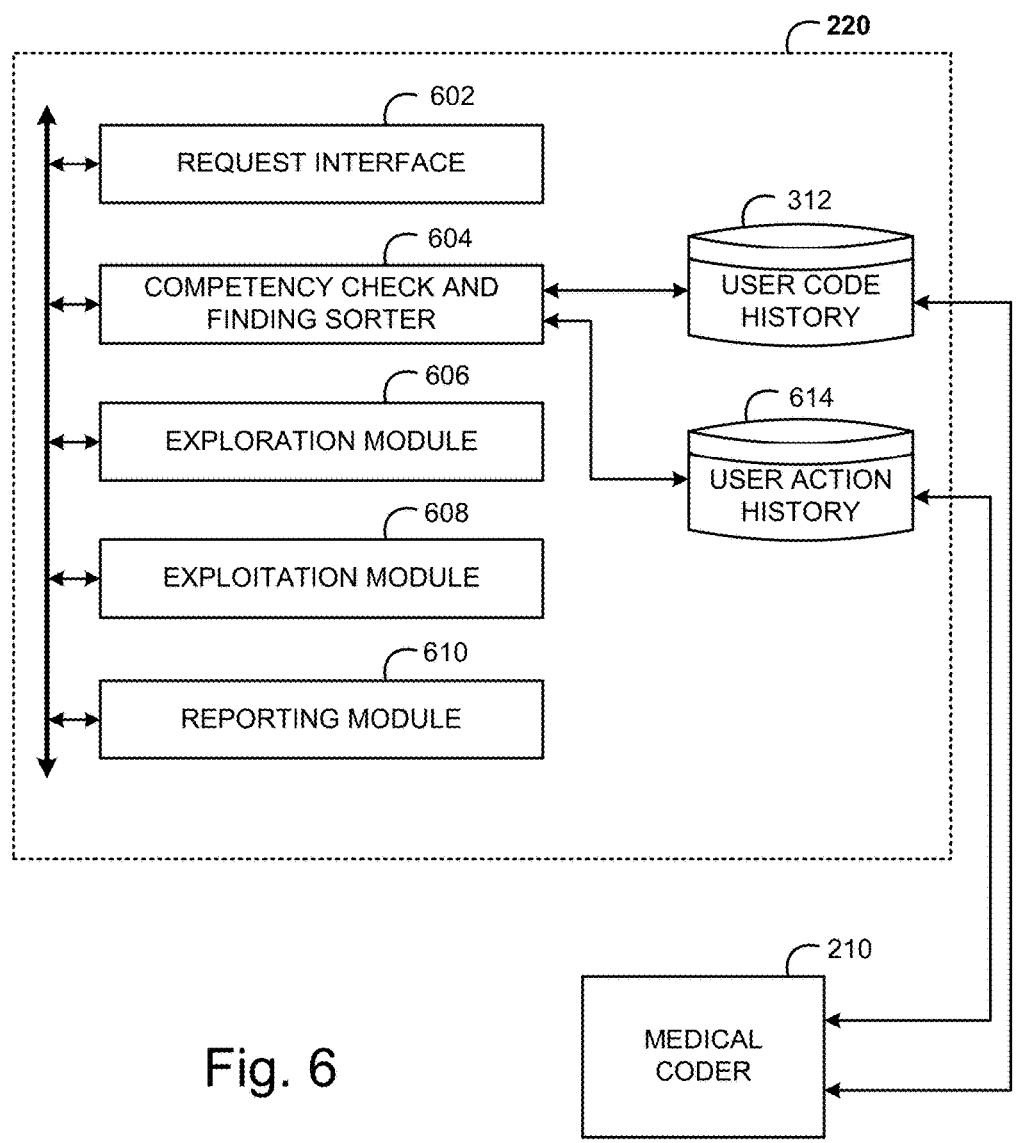
FIG. 6 shows an exemplary embodiment of the medical coder sorter, in accordance with an embodiment.

Turning to FIG. 6, a more detailed illustration of the medical coder sorter 220 is provided. Here it can be seen that the medical coder sorter 220 include a request interface 602, a competency check and finding sorter module 604, an exploration module 606, and exploitation module 608 and a reporting module 610. These subsystems may be logically or physically coupled within the medical coder sorter 220. The medical coder sorter 220 may also include, or have access to, databases of user coding history and recent user action history, 312 and 614 respectively. These databases are compiled using information generated from monitoring the medical coder 210.

It is often desirable for medical records to be routed to human coders in order to provide quality assurance for the medical record checking. In particular, when a confidence interval is low, or some other metric is met (for example the condition classifier identifies a condition which is often miscoded) the medical record may be routed through human coders to ensure accuracy of code submissions. The medical coder sorter 220 may be employed, in these embodiments, to ensure routing is performed efficiently.

The medical coder sorter 220 may work on a response model in which the client (often the clinical coder) requests a piece of work (also referred to as a finding or opportunity), or as identified above where the automated medical record review requires human quality assurance. The request includes the user's identification and the user's role. The medical coder sorter 220 accesses the coding history for the user. This coding history may be stored as a series of records in a database (as illustrated), or may be maintained as a state for the user. Further previous actions of the user may also be collected. Previous actions include any action taken by the user regarding the finding that was given previously by the medical coder sorter 220.

In response to the request the medical coder sorter 220 determines if it is in an exploratory or exploitation mode. Exploration refers the ability to explore the scope of the findings to estimate the parameters that control the coding, which may be employed to generate coder profiles. One way to undergo exploration would be to send a coder findings for which the coding is known (either as a standard or in comparison to other coders). The coder's responses may then be compared to the known values for the finding in order to measure parameters that influence the coder or coding. Alternately, randomized findings may be selected to generate metrics regarding the user.

Exploitation refers to the ability to select a finding for the user which maximizes one, or a combination of, factors. These factors may include, but are not limited to, energy, expected value per unit of time, predictive measure of coder's performance and higher level rules. Higher level rules may include user configurable rules such as recoding of suspect items, etc. Energy, as used herein, is defined as the probability of acceptance of the code multiplied by the prevalence of the code. The predictive measure of the coder's performance may include historical measures of how often the user's output is in disagreement with that of another coder.

The medical coder sorter 220 thus determines, based upon a percentage of time whether exploration or exploitation is desired. Additionally, a determination may be made as to whether the user is competent to continue coding. If the user is competent, the medical coder sorter 220 selects a finding based upon the exploration or exploitation criteria, and provides the finding, along with any evidence for it, to the user.

The medical coder sorter 220 may also generate metrics based upon user activity, which is used to populate the historical databases, and to generate reports.

Figure 7:
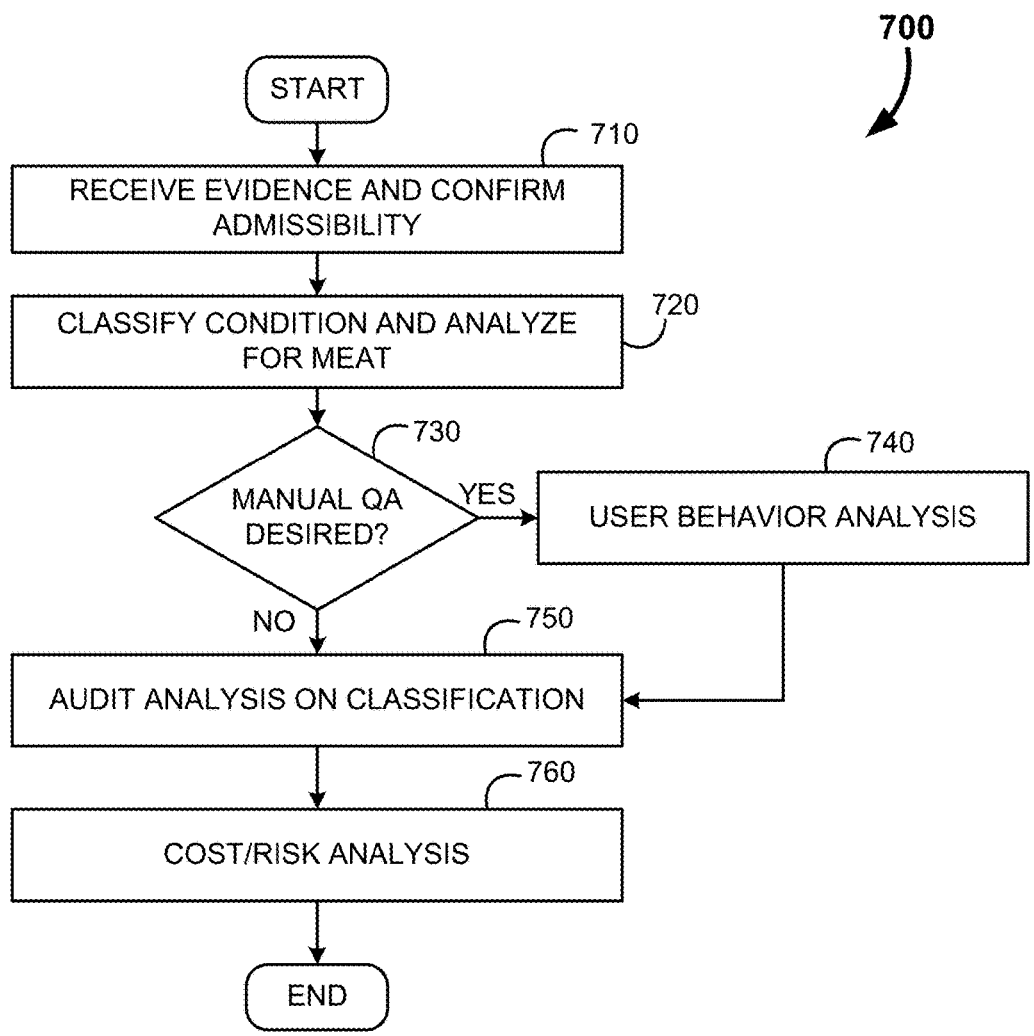
FIGS. 7-13 show flow charts for the process of efficiently reviewing medical charts, in accordance with an embodiment.

Now that the systems for the medical information management system have been disclosed, attention will be turned toward methods of processing medical records. In order to facilitate this discussion, FIG. 7 is provided which illustrates the process for medical record checking, shown generally at 700, in accordance with some embodiments. In this example process, the medical records are first received and the admissibility of the medical records is confirmed (at 710). As previously noted, this review may be performed in a live manner, or may be performed in a batch wise manner based upon number of medical records to be analyzed, or based upon a schedule.

Figure 8:
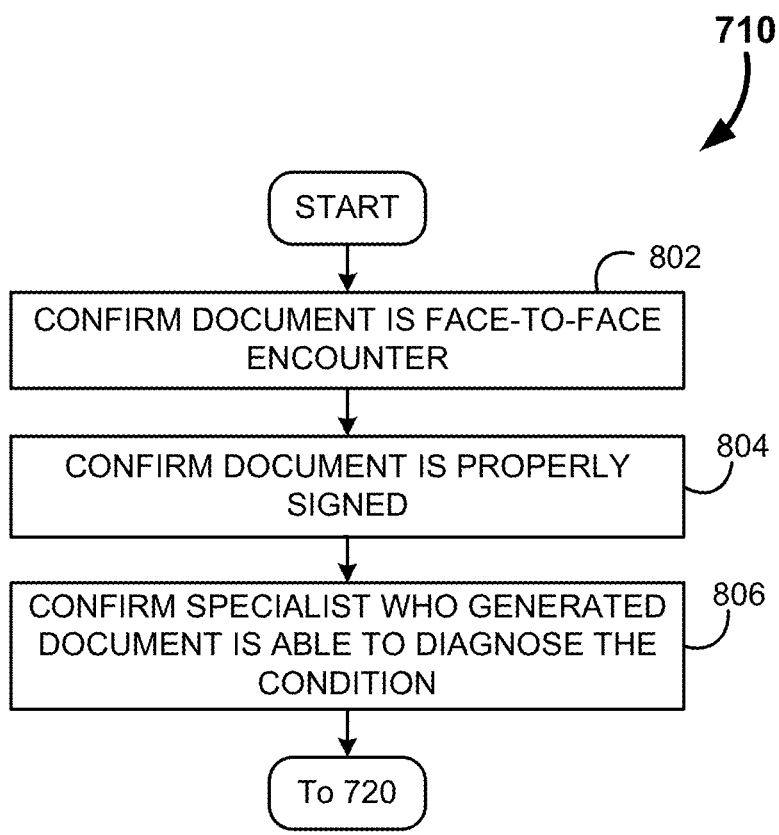

FIG. 8 provides a more detailed illustration of the determination of medical record admissibility. In this example sub process, the medical record is confirmed as a face-to-face encounter (at 802), confirmation of signature is made (at 804), and the specialist is confirmed to have the authority to generate the diagnosis (at 806). As previously stated, these admissibility confirmations may utilize any of metadata, keyword identification, contextual analysis, and image recognition.

Figure 9:
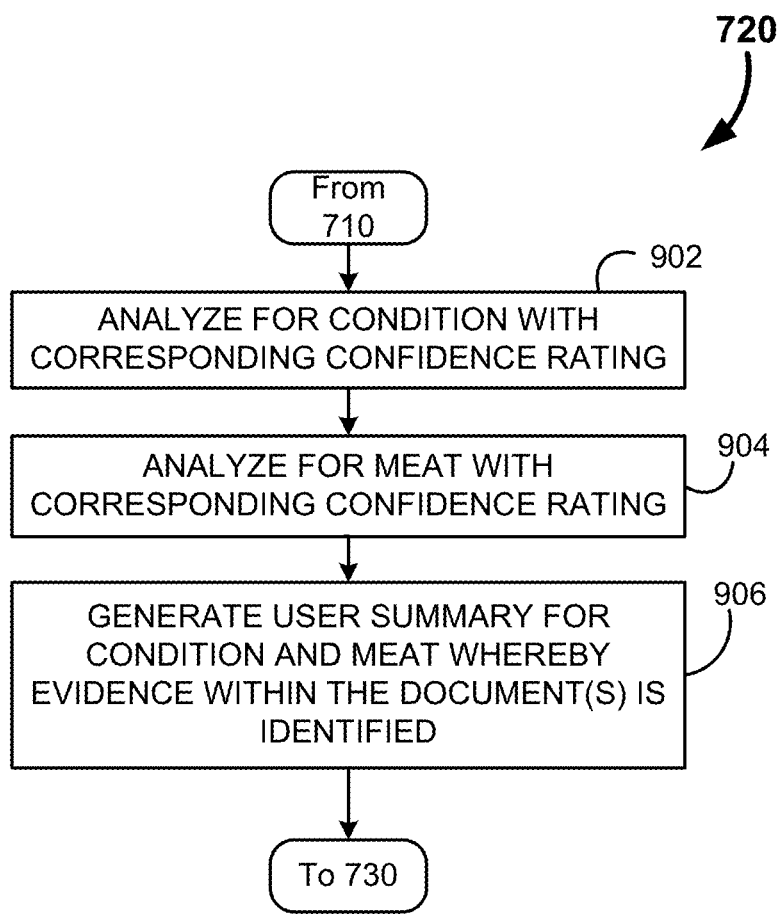

Returning to FIG. 7, after the record is deemed admissible, the condition is classified for the record, as well as MEAT is classified for each record (at 720). FIG. 9 provides a more detailed flow diagram for this classification step. Initially, a condition is identified and a corresponding confidence is generated (at 902). Next, the MEAT is identified within each document, and likewise a corresponding confidence is generated (at 904). Classification of condition and MEAT includes basic keyword matches, as well as higher dimensional contextual analysis.

A summary of the condition and MEAT is generated for user consumption (at 906) wherein the condition and MEAT evidence within the document is clearly identified. Often this identification includes highlighting of pertinent information for the user. In some embodiments, different highlighting colors may be employed to identify different data that the evidence corresponds to, and further the degree of evidence value. For example, a slightly elevated level of blood sugar may be evidence of diabetes, but dramatically elevated levels may be much stronger evidence. This evidence may be shaded accordingly. Likewise, evidence for treatment (as part of MEAT classification) may be highlighted in an entirely separate color.

Returning to FIG. 7, after classification a determination may be made whether to have manual quality assurance of the medical recorded check (at 730). This quality assurance determination may be made on a random basis, or may be in response to factors within the medical record. For example, medical records which are classified, but have relatively low confidence scores for the condition and MEAT analysis may be candidates for human quality assurance. Likewise, records for a particular condition, generated by a particular physician, within a specific geographic location, etc. may likewise be configured to be routed to a human for additional review.

Figure 10:
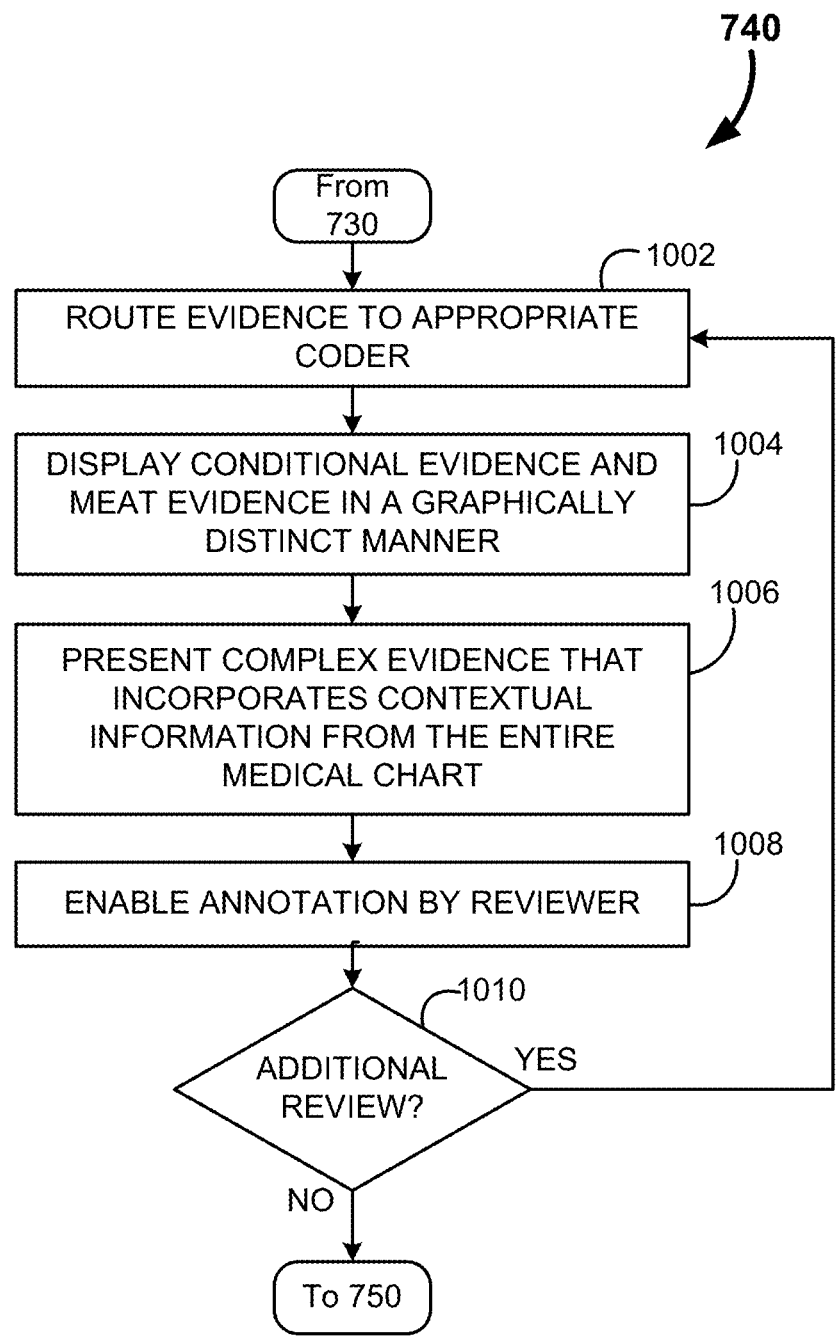

If human review is not desired, then the process proceeds to an audit analysis (at 750). However, if human quality assurance is desired, then the record can be routed for user behavior analysis (at 740). User behavior analysis is described in greater detail in relation to FIG. 10. In this example sub process, the evidence is first routed to an appropriate coder (at 1002). This routing may be done randomly, or via a coder sorting system.

Figure 11:
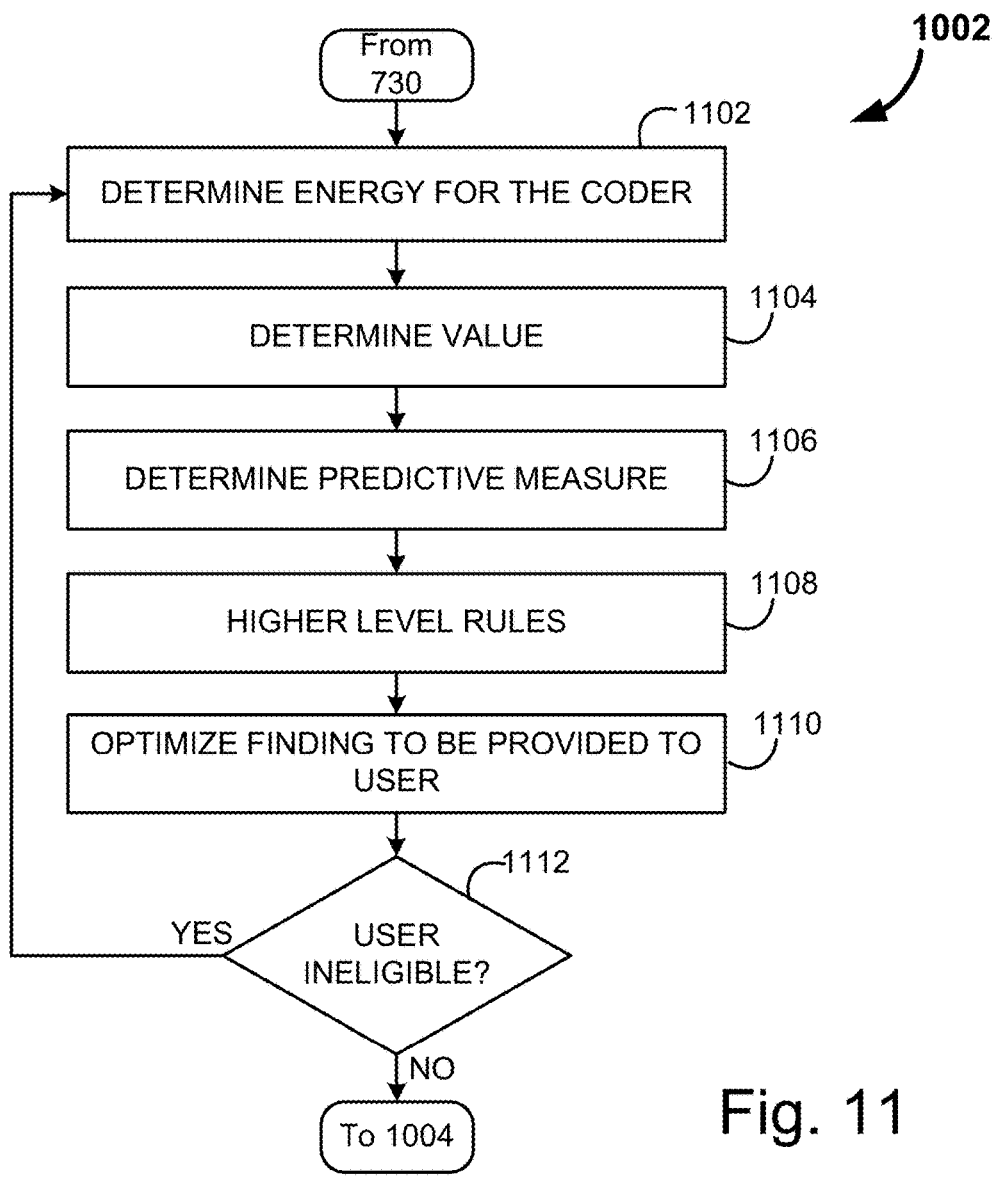

FIG. 11 provides an example process flow diagram for the sorting of findings. The pertinent records for a user are sought. Pertinent records include coding history for the user and previous actions of the user. The energy for the coder (acceptance ratio) is determined based upon historical actions (at 1102). Likewise, the amount of money a particular user is likely to generate per a period of time is determined (at 1104). For example, a coder may be much faster than other coders, and may therefore clear a larger sum in a period of time. Alternatively, a coder may identify larger valued codes that are often overlooked by other coders.

Next, the predictive ability for the user is determined (at 1106). The predictive measure may include how often the user's work product is recoded in historical records during quality assurance. Additionally, higher level rules can be quantified (at 1108), such as identifying findings that are suspect and flagging them for reassessment. Higher level rules may be created, read, updated and deleted by a user, administrator or other entity to ensure peak performance of the sorting.

One or more of these criteria may then be optimized for in order to match a finding to the user which meets the goal (at 1110). For example, if quality of codings has been at issue, the system may maximize the recoding of suspect records (higher level rule) with users who have high predictive accuracy. Thus, if the user were to have high accuracy historically, they would receive a finding that is suspect. However, if the user has less than optimal accuracy, but historically generates codes for findings very quickly, suspect records may be held back and rather simpler finding may be provided to the user. In this manner the system may determine what the user is good at, and present findings which most closely match the user's strengths in order to maximize coding efficiency.

Figure 12:
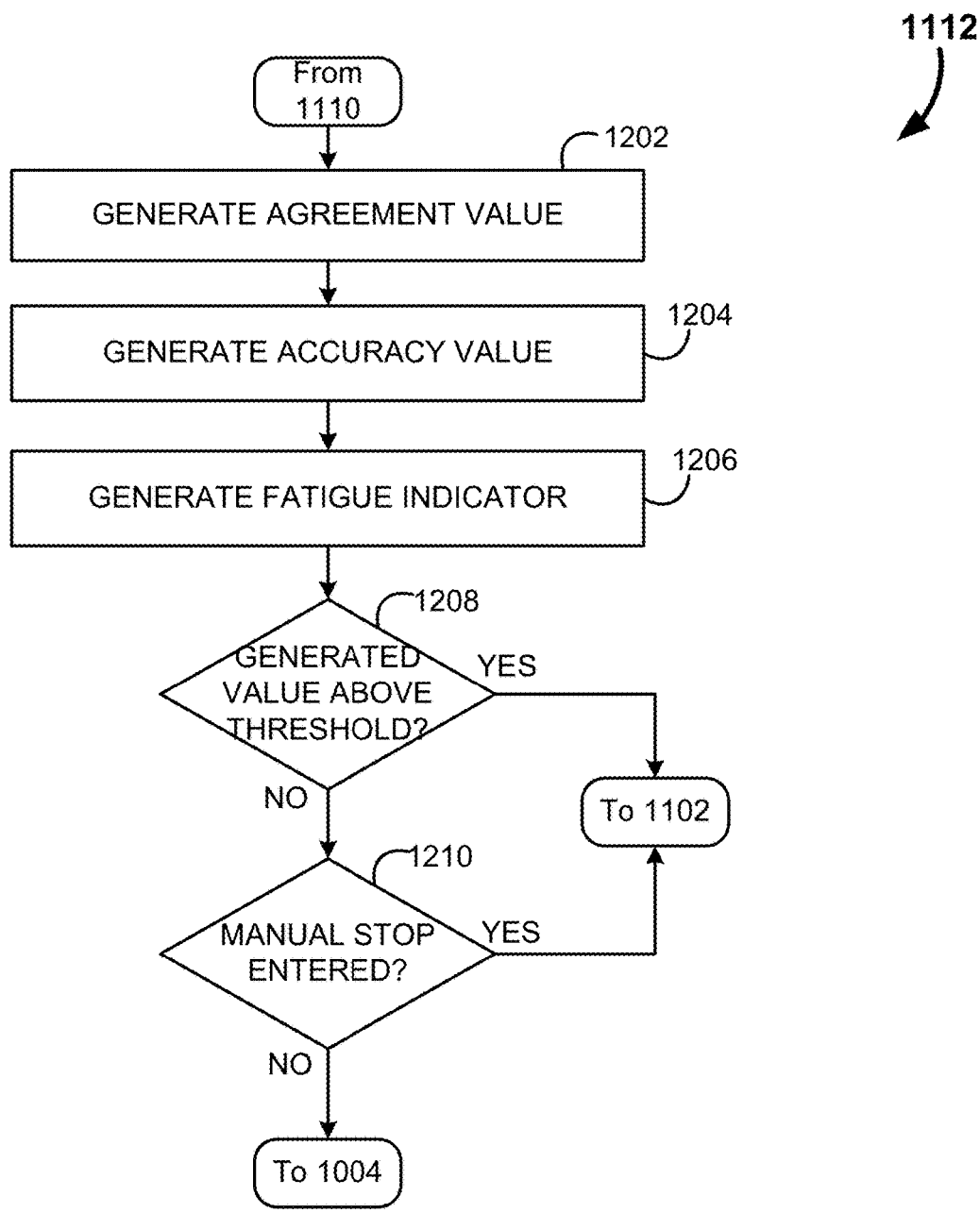

Lastly, a determination is made whether the user is not competent to continue coding (at 1112). FIG. 12 provides a more detailed process flow diagram for this decision making process. The system may generate an agreement value for the user (at 1202). Agreement value may consist of how often the user's coding results are in agreement with the coding results of other users. Likewise, an accuracy value for the user may be generated (at 1204). Accuracy values indicate how often the user properly identifies a finding and assigns the accurate code to the finding. Further, a fatigue indicator is generated for the user (at 1206). Fatigue may manifest in a number of ways, including the duration of time the user has been continuously coding, rapid increase in error rates, longer time spent on findings before assigning codes, or trivial error rates.

If any of these values are above a desired threshold (at 1208), then the user may be determined to be incompetent for further coding. Likewise, there may be a manual interrupt (at 1210) which allows a manager, administrator or other party to discontinue findings being sent to a coder.

Returning to FIG. 11, if a stop condition is met, the process ceases to provide findings to the coder, and the process returns to the beginning where the energy for a new coder is determined. Otherwise, if the user is determined to be eligible, the record is routed to that user.

Returning to FIG. 10, after an appropriate coder has been identified, the conditional evidence and MEAT evidence is presented to the user in a graphically distinct manner (at 1004). As previously noted, this graphical display may include highlighting the evidence for each finding using a differing color based upon evidence type and strength.

Complex evidence that incorporates contextual information from multiple locations in an entire medical chart may also be displayed (at 1006) in a summary fashion, or otherwise easily digestible manner. By presenting the evidence to the user in such a manner, the human review process may be significantly streamlined since the user can be immediately directed to pertinent information. In addition to efficient categorization and presentation of data to the user, the reviewer may have the option to accept or reject the findings by the condition classifier and the MEAT classifier. Further, the system may also enable the user to annotate the medical records (at 1008). Annotation may include reviewer highlighting of additional evidence, addition of comments, or flagging of evidence for review.

Figure 15:
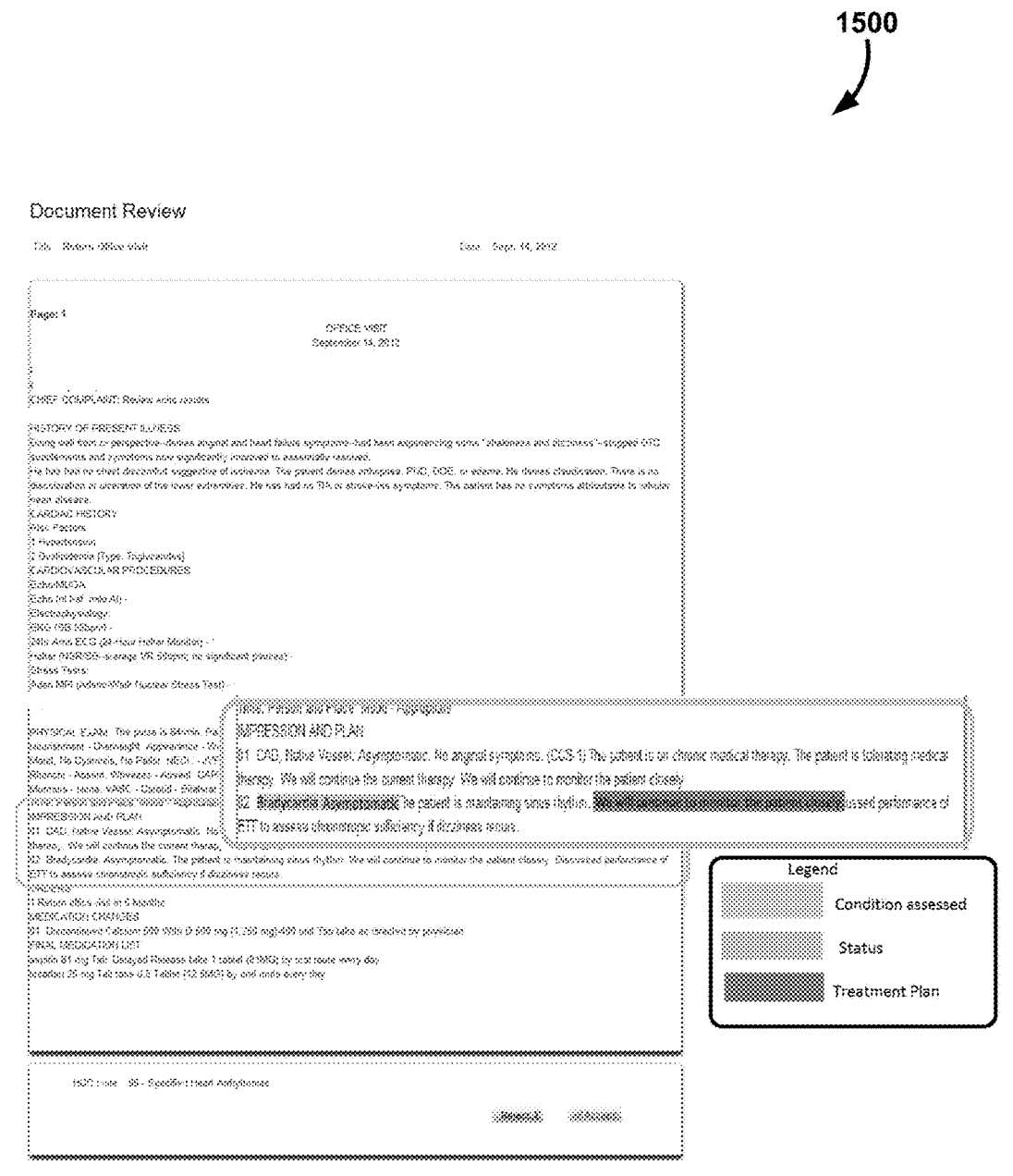

Turning briefly to FIG. 15, an example screenshot is provided for the display of a record to a reviewer, seen generally at 1500. In this example screenshot, a medical record from an office visit is provided. Evidence for a condition is enhanced for the viewer, and the condition assessment, evaluation, and treatment are each highlighted for the coder's review. A legend is likewise provided to the coder. At the bottom of the screenshot, the coder has the ability to accept the conditional finding, or reject it.

Returning to FIG. 10, after the reviewer has completed the review of the medical record, and inquiry is made whether to route the record to additional reviewers (at 1010). This decision to route may include a weighted determination based upon confidence values, agreement by the reviewer, characteristics of the medical record (condition, geography it was generated in, physician, etc.) or whether the reviewer flagged anything in it for follow-up review. If additional review is desired, the process may return to where a new reviewer is selected. Otherwise it can return to FIG. 7, where audit analysis is performed on the classifications (at 750).

Figure 13:
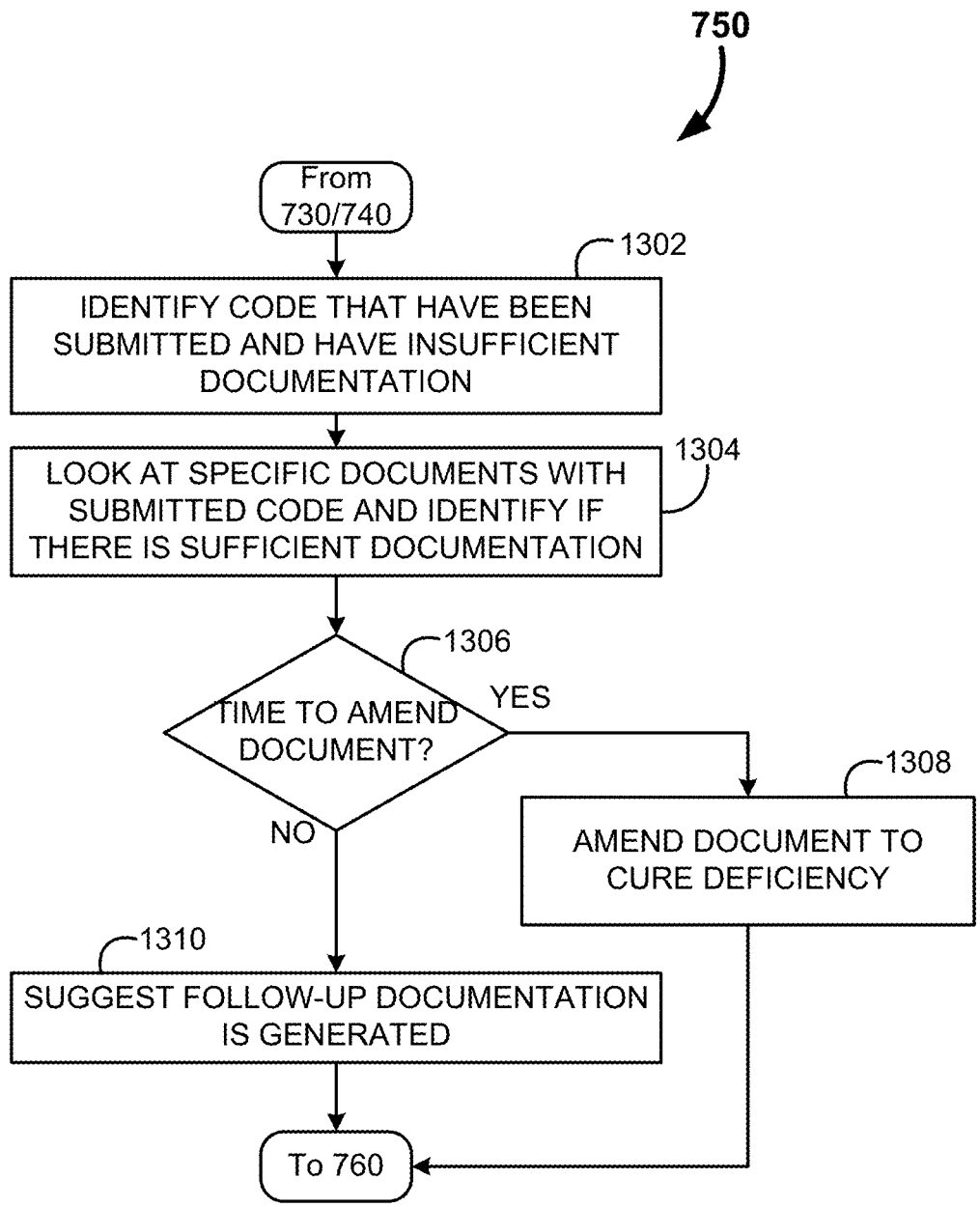

FIG. 13 provides a more detailed example for the audit analysis. Auditing may be performed live, or in batches, as previously discussed. In this process, the codes that have been submitted to a risk assessment authority (Medicare, HHS, etc.) are identified which have insufficient evidence within the medical records (at 1302). Likewise, specific documents which are associated with submitted codes may be analyzed to determine if sufficient evidence is present (at 1304). Sufficiency of evidence may be determined if a condition is identified, all aspects of MEAT have been identified in each document, and if the confidence scores are above some minimum threshold. Likewise, user review results may be factored into the determination of document insufficiency.

Next a determination is made whether there is time to amend the documents (at 1306), and if so, the document may be amended to cure the deficiency (at 1308). Often this curing involves contacting the individual who generated the record, and informing them of the deficiency. Often the individual may correct the issue by recalling assessments, or merely rewording the language.

However, if there is not sufficient time to amend the document, or if the document cannot be cured via a simple amendment, then a suggestion for a follow-up document is generated, when practical (at 1310). For example, if evidence exists for a pathology, but the assessment was never incorporated into a document, the patient may be requested for a follow-up clinical visit to confirm the diagnosis.

At a minimum, the results of the insufficiencies may be provided to the customer (insurance provider, healthcare provider, physician, etc.) in order to hone internal processes, and avoid similar audit mistakes in the future.

Returning to FIG. 7, after audit analysis, cost/risk analysis may be performed (at 760). As previously discussed, healthcare codes are actually poor indicators of the cost/risk present in a patient population. By employing MEAT classifications and condition classification, as well as other contextual metrics, more accurate measures of risk and costs may be predicted by correlating a cost surrogate with a measure of importance. These costs may be presented as direct costs to the customer (insurance company, healthcare provider, etc.) or as indirect costs.

An important feature for routing of medical records and the generation of meaningful costs and risks is the availability of customer and coder profiles. These profiles, as previously discussed, indicate coder propensities and behaviors, and provide information regarding the customer (healthcare provider, organization, insurance company, etc.).

Figure 14:
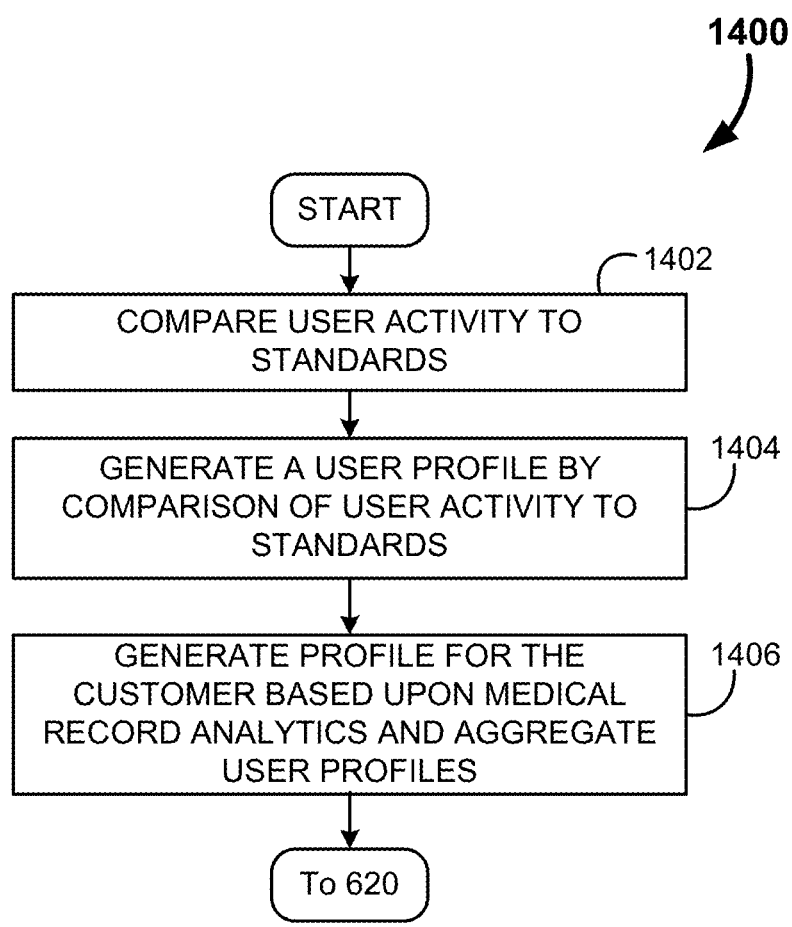
FIG. 14 shows a flow chart for the process of generating customer profiles, in accordance with some embodiment.

The generation of profiles, as previously touched upon, relies upon comparing coder behavior to standards, and combining this information with statistical metrics. FIG. 14 (at 1400) provides a method for generating such profiles. Initially, user activity is compared to set standards (at 1402). These may be global standards, sets of user averages, customer-specific gold standards, application-specific gold standards, and the like. These standards may be interspersed within the coding activity of users, and the results generated by the user can be compared against the standards. Customer-specific standards may be developed by having a customer expert use application. These comparisons result in the generation of a profile for the user (at 1404).

This comparison to standards enables the quantification of under and over coding, performance variation over time, types of data, application domain, etc. It also enables the ability to compare coders across multiple organizations, and likewise, the coding quality of one organization may be compared against other organizations. Organization level profiles are generated (at 1406) by aggregating coder profiles, and adding additional analytics, such as pathology frequency, process waste and the like.

Figure 16A:
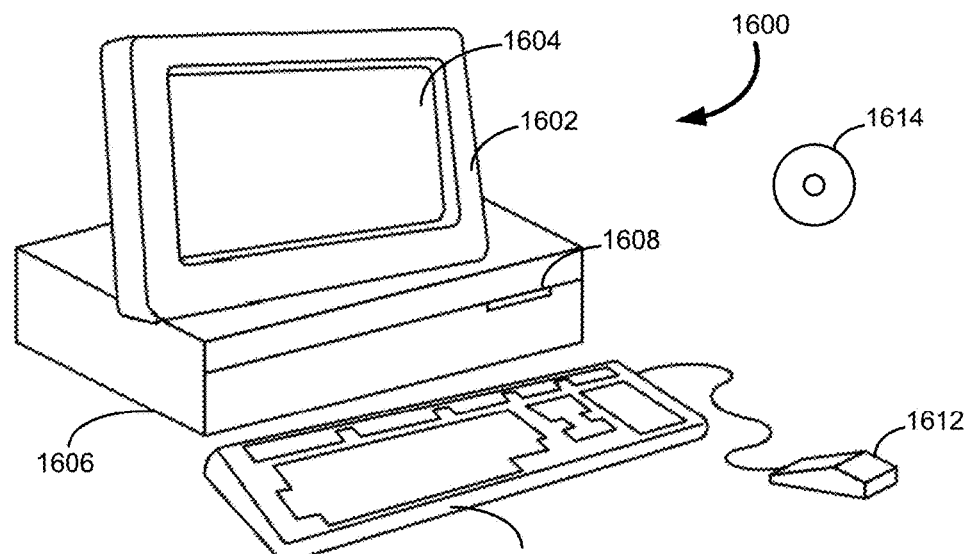
FIGS. 16A and 16B are example illustrations of a computer system capable of embodying the current invention.
Figure 16B:
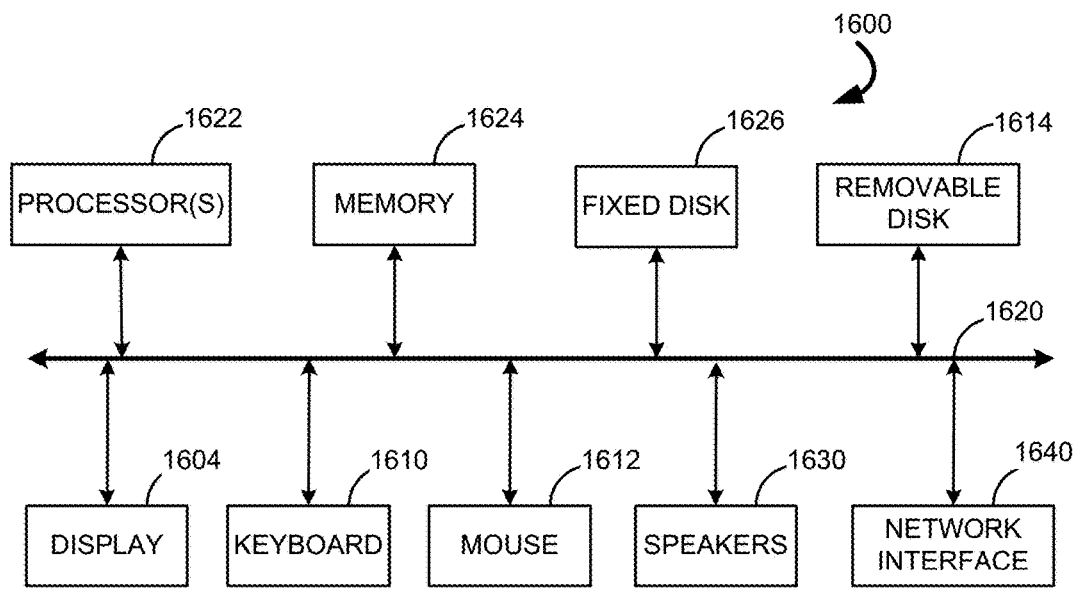

FIGS. 16A and 16B illustrate a Computer System 1600, which is suitable for implementing embodiments of the present invention. FIG. 16A shows one possible physical form of the Computer System 1600. Of course, the Computer System 1600 may have many physical forms ranging from a printed circuit board, an integrated circuit, and a small handheld device up to a huge super computer. Computer system 1600 may include a Monitor 1602, a Display 1604, a Housing 1606, a Disk Drive 1608, a Keyboard 1610, and a Mouse 1612. Disk 1614 is a computer-readable medium used to transfer data to and from Computer System 1600.

FIG. 16B is an example of a block diagram for Computer System 1600. Attached to System Bus 1620 are a wide variety of subsystems. Processor(s) 1622 (also referred to as central processing units, or CPUs) are coupled to storage devices, including Memory 1624. Memory 1624 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1626 may also be coupled bi-directionally to the Processor 1622; it provides additional data storage capacity and may also include any of the computer-readable media described below. Fixed Disk 1626 may be used to store programs, data, and the like and is typically a secondary storage medium (such as a hard disk) that is slower than primary storage. It will be appreciated that the information retained within Fixed Disk 1626 may, in appropriate cases, be incorporated in standard fashion as virtual memory in Memory 1624. Removable Disk 1614 may take the form of any of the computer-readable media described below.

Processor 1622 is also coupled to a variety of input/output devices, such as Display 1604, Keyboard 1610, Mouse 1612 and Speakers 1630. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1622 optionally may be coupled to another computer or telecommunications network using Network Interface 1640. With such a Network Interface 1640, it is contemplated that the Processor 1622 might receive information from the network, or might output information to the network in the course of performing the above-described medical record reviewing. Furthermore, method embodiments of the present invention may execute solely upon Processor 1622 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a health information management system, a computerized method for processing medical records, comprising:
   receiving at least one medical record;
   processing the at least one medical record by indexing and semantic meta-tagging to alter the at least one medical record format, embedding information in metadata;
   providing the processed at least one medical record to an analytics layer of a data storage architecture;
   generating, using a processor, a condition based upon at least one medical record of the processed at least one medical record, wherein the condition includes a first confidence value;
   determining admissibility of each medical record by confirming that an encounter associated with the medical record was face-to-face, signed, and by an admissible specialist, wherein the confirming the encounter is face-to-face includes contextual analysis of confirmation statements, presence of a procedure that requires patient attendance, and metadata, and wherein the confirming the medical record is signed includes an image recognition algorithm, and wherein the confirming the admissible specialist includes cross referencing the condition against a physician performing the diagnosis responsive to a table of allowable diagnoses for the specialty of the physician;
   contacting the physician, a healthcare provider or insurance company when the medical record is inadmissible with a suggestion for correction;
   scheduling an examination of the patient to correct the inadmissible record; and
   generating a MEAT determination for each medical record, wherein the MEAT determination includes a second confidence value, and further wherein the MEAT determination includes identifying a monitor component, and evaluation component, an assessment component and a treatment component.

2. The method of claim 1, further comprising determining if human quality assurance is required.

3. The method of claim 2, wherein the determination of human quality assurance is based upon at least one of the first confidence value, the second confidence value, and medical record attributes.

4. The method of claim 3, wherein the medical record attributes include at least one of the condition, geography of the medical record, physician who generated the medical record, insurance type, and patient history.

5. The method of claim 2, further comprising routing the medical record to a coder for user behavior analysis.

6. The method of claim 5, wherein the routing compares coder attributes to goals and optimizes for outcome.

7. The method of claim 1, wherein generating the condition and MEAT determination includes keyword and contextual analysis.

8. The method of claim 5, further comprising generating a summary of the condition and MEAT determination for the coder, wherein the summary includes graphically highlighting evidence within each medical record for the coder.

9. The method of claim 1, further comprising generating an audit analysis by identifying codes which have been submitted and have insufficient evidence, and analyzing specific medical records with submitted codes to determine if sufficient evidence is present.

10. The method of claim 9, further comprising determining if there is time to amend the medical records, and if so providing a suggestion to amend the medical records to cure deficiencies.

11. The method of claim 10, further comprising providing a suggestion for a follow-up with the patient when the medical records cannot be amended.

12. The method of claim 1, further comprising generating cost metric for the patient based upon the condition and MEAT determination.

13. A health information management system for processing medical records comprising:
   an interface configured to receive at least one medical record;
   a processor for processing the at least one medical record by indexing and semantic meta-tagging to alter the at least one medical record format, embedding information in metadata;
   a database including an analytics layer for receiving the processed at least one medical record;
   the processor further configured to generate a condition based upon at least one medical record of the processed at least one medical record, wherein the condition includes a first confidence value, and
   determine admissibility of each medical record by confirming that an encounter associated with the medical record was face-to-face, signed, and by an admissible specialist, wherein the confirming the encounter is face-to-face includes contextual analysis of confirmation statements, presence of a procedure that requires patient attendance, and metadata, and wherein the confirming the medical record is signed includes an image recognition algorithm, and wherein the confirming the admissible specialist includes cross referencing the condition against a physician performing the diagnosis responsive to a table of allowable diagnoses for the specialty of the physician;
   the interface for contacting the physician, a healthcare provider or insurance company when the medical record is inadmissible with a suggestion for correction; and
   the processor further configured for scheduling an examination of the patient to correct the inadmissible record, and
   generate a MEAT determination for each medical record, wherein the MEAT determination includes a second confidence value, and further wherein the MEAT determination includes identifying a monitor component, and evaluation component, an assessment component and a treatment component.

14. The system of claim 13, further comprising the processor configured to determine if human quality assurance is required.

15. The system of claim 14, wherein the determination of human quality assurance is based upon at least one of the first confidence value, the second confidence value, and medical record attributes.

16. The system of claim 15, wherein the medical record attributes include at least one of the condition, geography of the medical record, physician who generated the medical record, insurance type, and patient history.

17. The system of claim 14, wherein the processor is further configured to route the medical record to a coder for user behavior analysis.

18. The system of claim 17, wherein the routing compares coder attributes to goals and optimizes for outcome.

19. The system of claim 13, wherein generating the condition and MEAT determination includes keyword and contextual analysis.

20. The system of claim 17, wherein the processor is further configured to generate a summary of the condition and MEAT determination for the coder, wherein the summary includes graphically highlighting evidence within each medical record for the coder.

21. The system of claim 13, further comprising the processor configured to generate an audit analysis by identifying codes which have been submitted and have insufficient evidence, and analyzing specific medical records with submitted codes to determine if sufficient evidence is present.

22. The system of claim 21, wherein the processor is further configured to determine if there is time to amend the medical records, and if so providing a suggestion to amend the medical records to cure deficiencies.

23. The system of claim 22, wherein the processor is further configured to provide a suggestion for a follow-up with the patient when the medical records cannot be amended.

24. The system of claim 13, further comprising the processor configured to generate a cost metric for the patient based upon the condition and MEAT determination.

* * * * *